US009233169B2

(12) United States Patent
Riggs-Sauthier et al.

(10) Patent No.: US 9,233,169 B2
(45) Date of Patent: *Jan. 12, 2016

(54) OLIGOMER-BIS-CHROMONYL COMPOUND CONJUGATES

(71) Applicant: NEKTAR THERAPEUTICS, San Francisco, CA (US)

(72) Inventors: Jennifer Riggs-Sauthier, San Francisco, CA (US); Bo-Liang Deng, San Ramon, CA (US)

(73) Assignee: Nektar Therapeutics, San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/627,370

(22) Filed: Feb. 20, 2015

(65) Prior Publication Data

US 2015/0157734 A1    Jun. 11, 2015

Related U.S. Application Data

(63) Continuation of application No. 12/989,074, filed as application No. PCT/US2009/002525 on Apr. 23, 2009.

(60) Provisional application No. 61/125,478, filed on Apr. 25, 2008.

(51) Int. Cl.
| | | |
|---|---|---|
| *A61K 31/35* | (2006.01) | |
| *C07D 311/00* | (2006.01) | |
| *A61K 47/48* | (2006.01) | |
| *A61K 31/353* | (2006.01) | |

(52) U.S. Cl.
CPC ......... *A61K 47/48215* (2013.01); *A61K 31/353* (2013.01)

(58) Field of Classification Search
CPC ............. A61K 47/48215; A61K 31/353
USPC .......................... 549/402; 514/456
See application file for complete search history.

(56) References Cited

U.S. PATENT DOCUMENTS

| | | |
|---|---|---|
| 3,419,578 A | 12/1968 | Fitzmaurice et al. |
| 5,672,662 A | 9/1997 | Harris et al. |
| 2005/0136031 A1 | 6/2005 | Bentley et al. |
| 2010/0094026 A1 | 4/2010 | Tanaka et al. |
| 2011/0112183 A1 | 5/2011 | Riggs-Sauthier et al. |

FOREIGN PATENT DOCUMENTS

| | | |
|---|---|---|
| WO | WO 02/098949 | 12/2002 |
| WO | WO 2005/058367 | 6/2005 |
| WO | WO 2007/052398 | 5/2007 |

OTHER PUBLICATIONS

Chen, et al., "Synthesis and Properties of ABA Amphiphiles," J. Org. Chem., vol. 64, pp. 6870-6873, (1999).
Nuki, et al., "The inhibition of mast cell degranulation in monkey gingiva by disodium cromoglycate," J. Periodontal Res., vol. 10, pp. 282-287, (1975).
PCT International Search Report corresponding to PCT Application No. PCT/US2009/002525 date of mailing Sep. 25, 2009.
PCT International Preliminary Report on Patentability corresponding to PCT Application No. PCT/US20009/002525 date of mailing Nov. 4, 2010.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003. (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003—$1^{st}$, (Jan. 2003).
NOF Corporation, PEG Derivatives, Phospholipid and Drug Delivery Materials for Pharmaceuticals, 27 pages, Catalogue 2003—$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives; Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).

*Primary Examiner* — T. Victor Oh

(57) ABSTRACT

The invention provides oligomer-bis-chromonyl compound conjugates. The conjugates of the invention, when administered by any of a number of administration routes, exhibits advantages over previously administered compounds.

8 Claims, No Drawings

OLIGOMER-BIS-CHROMONYL COMPOUND CONJUGATES

CROSS REFERENCE TO RELATED APPLICATIONS

This application is a Continuation of U.S. patent application Ser. No. 12/989,074, filed 25 Jan. 2011, which is a 35 U.S.C. §371 application of International Application No. PCT/US2009/002525, filed 23 Apr. 2009, designating the United States, which claims the benefit of priority under 35 U.S.C. §119(e) to U.S. Provisional Patent Application Ser. No. 61/125,478, filed 25 Apr. 2008, all of which are incorporated herein by reference in their entireties.

FIELD OF THE INVENTION

This invention provides (among other things) chemically modified bis-chromonyl compounds that possess certain advantages over bis-chromonyl compounds lacking the chemical modification. The chemically modified bis-chromonyl compounds described herein relate to and/or have application(s) in (among others) the fields of drug discovery, pharmacotherapy, physiology, organic chemistry and polymer chemistry.

BACKGROUND OF THE INVENTION

Bis-chromonyl compounds are pharmacologically active compounds in which two moieties structurally related to chromone are linked together, often through a methylene-containing bridge. The chemical structure of chromone is shown below.

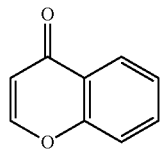

chromone

One of the best known bis-chromonyl compounds is cromolyn sodium (sometimes referred to as "cromoglycate"), which is disodium 5,5'-((2-hydroxytrimethylene)dioxy)bis (4-oxo-4H-1 benzopyran-2-carboxylate). Cromonlyn sodium has been reported to inhibit mast cell degranulation of monkey gingiva. See Nuki et al. (1975) J. Periodontal. Res. 10:282-287. As such, cromolyn sodium is often used as an inhaled anti-inflammatory agent for the preventive management of asthma.

Marketed forms of cromolyn sodium include the following: RYNACROM® and NASALCROM® brands of cromolyn sodium nasal spray for allergic rhinitis; INTAL® brand of cromolyn sodium inhaler for preventive management of asthma; OPTICROM®, OPTREX ALLERGY® and CROLOM® brands of cromolyn sodium eye drops for allergic conjunctivitis; and GASTROCOM® brand of cromolyn sodium for the treatment of mastocytosis, dermatographic urticaria, and ulcerative colitis.

Cromolyn (in contrast to cromolyn sodium) and other non-salt forms of bis-chromonyl compounds are poorly absorbed from the gastrointestinal tract, often with no more than 1% of an administered dose being absorbed by humans following oral administration, the remainder being excreted in the feces. As such, it would be advantageous to (among other things) improve the overall oral bioavailability of bis-chromonyl compounds The present invention seeks to address this and other needs in the art by providing (among other things) a conjugate of a water-soluble and non-peptidic oligomer and bis-chromonyl compound.

SUMMARY OF THE INVENTION

In one or more embodiments of the invention, a compound is provided, the compound comprising a residue of a bis-chromonyl compound covalently attached via a stable or degradable linkage to a water-soluble, non-peptidic oligomer.

In one or more embodiments of the invention, a compound is provided, the compound comprising a residue of a bis-chromonyl compound covalently attached via a stable or degradable linkage to a water-soluble, non-peptidic oligomer, wherein the bis-chromonyl compound has a structure encompassed by the following formula:

Formula I

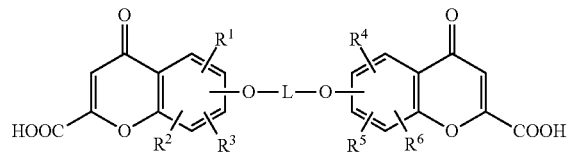

wherein:

$R^1$ is hydrogen, hydroxy, halo, lower alkyl (including substituted lower alkyl), and lower alkoxy (including substituted lower alkoxy);

$R^2$ is hydrogen, hydroxy, halo, lower alkyl (including substituted lower alkyl), and lower alkoxy (including substituted lower alkoxy);

$R^3$ is hydrogen, hydroxy, halo, lower alkyl (including substituted lower alkyl), and lower alkoxy (including substituted lower alkoxy);

$R^4$ is hydrogen, hydroxy, halo, lower alkyl (including substituted lower alkyl), and lower alkoxy (including substituted lower alkoxy);

$R^5$ is hydrogen, hydroxy, halo, lower alkyl (including substituted lower alkyl), and lower alkoxy (including substituted lower alkoxy);

$R^6$ is hydrogen, hydroxy, halo, lower alkyl (including substituted lower alkyl), and lower alkoxy (including substituted lower alkoxy); and L is an alkylene-containing linkage that may be one or the more of the following: saturated or unsaturated; substituted or unsubstituted; straight or branched; and interrupted by one or more of the moieties selected from the group consisting of carbocyclic rings, oxygen-containing heterocyclic rings, oxygen atoms, and carbonyl groups.

Exemplary compounds of the invention include those having the following structure:

Formula I-C

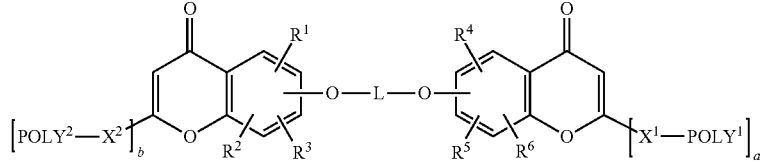

wherein:

$R^1$ is hydrogen, hydroxy, halo, lower alkyl (including substituted lower alkyl), and lower alkoxy (including substituted lower alkoxy);

$R^2$ is hydrogen, hydroxy, halo, lower alkyl (including substituted lower alkyl), and lower alkoxy (including substituted lower alkoxy);

$R^3$ is hydrogen, hydroxy, halo, lower alkyl (including substituted lower alkyl), and lower alkoxy (including substituted lower alkoxy);

$R^4$ is hydrogen, hydroxy, halo, lower alkyl (including substituted lower alkyl), and lower alkoxy (including substituted lower alkoxy);

$R^5$ is hydrogen, hydroxy, halo, lower alkyl (including substituted lower alkyl), and lower alkoxy (including substituted lower alkoxy);

$R^6$ is hydrogen, hydroxy, halo, lower alkyl (including substituted lower alkyl), and lower alkoxy (including substituted lower alkoxy);

L is an alkylene-containing linkage that may be one or the more of the following: saturated or unsaturated; substituted or unsubstituted; straight or branched; and interrupted by one or more of the moieties selected from the group consisting of carbocyclic rings, oxygen-containing heterocyclic rings, oxygen atoms, and carbonyl groups;

(a) is either zero or one, with the caveat that when (a) is zero, —$X^1$—$POLY^1$ is —COOH;

(b) is either zero or one; with the caveat that when (b) is zero, —$X^2$—$POLY^2$ is —COOH;

with the provisio that at least one of (a) and (b) is one;

$X^1$, when present, is a spacer moiety (preferably —C(O)—O—);

$X^2$, when present, is a spacer moiety (preferably —C(O)—O—);

$POLY^1$, when present, is a water-soluble, non-peptidic oligomer; and $POLY^2$, when present, is a water-soluble, non-peptidic oligomer.

In one or more embodiments of the invention, a dosage form is provided, the dosage form comprising a compound comprising a residue of a bis-chromonyl compound covalently attached via a stable or degradable linkage to a water-soluble, non-peptidic oligomer.

In one or more embodiments of the invention, a method is provided, the method comprising covalently attaching a water-soluble, non-peptidic oligomer to a bis-chromonyl compound.

In one or more embodiments of the invention, a method is provided, the method comprising administering a compound comprising a residue of a bis-chromonyl compound covalently attached via a stable or degradable linkage to a water-soluble, non-peptidic oligomer.

These and other objects, aspects, embodiments and features of the invention may become more fully apparent when read in conjunction with the following detailed description.

DETAILED DESCRIPTION OF THE INVENTION

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated— either in a pattern or randomly—to form the oligomer. Preferred oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though the oligomer may contain distinct end capping moieties or functional groups, e.g., for conjugation. PEG oligomers for use in the present invention will comprise one of the two following structures: "—$(CH_2CH_2O)_n$-" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable (n) ranges from 1 to 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like.

"Branched," in reference to the geometry or overall structure of an oligomer, refers to an oligomer having two or more polymer "arms" that extend from a branch point.

"Forked," in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, thiolesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single (i.e., the same) molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the residue of the bis-chromonyl compound. A composition comprised of monodisperse conjugates may, however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the residue of the bis-chromonyl compound. A composition comprised of bimodal conjugates may, however, include one or more nonconjugate substances such as solvents, reagents, excipients, and so forth.

A "bis-chromolyn compound" is broadly used herein to refer to an organic, inorganic, or organometallic compound typically having a molecular weight of less than about 1000 Daltons (and typically less than 525 Daltons) and having some degree of mast cell stabilization activity.

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier ("BBB"); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate" provides a measure of a compound's ability to cross a biological membrane, such as the blood-brain barrier ("BBB"). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or may be determined by one of ordinary skill in the art.

"Alkyl" refers to a hydrocarbon chain ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Pharmaceutically acceptable excipient" or "pharmaceutically acceptable carrier" refers to component that may be included in the compositions of the invention causing no significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, and patient considerations, and can readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a residue of a bis-chromonyl compound covalently attached via a stable or degradable linkage to a water-soluble and non-peptidic oligomer.

In one or more embodiments of the invention, a compound is provided, the compound comprising a residue of a bis-chromonyl compound covalently attached via a stable or degradable linkage to a water-soluble, non-peptidic oligomer, wherein the bis-chromonyl compound has a structure encompassed by the following formula:

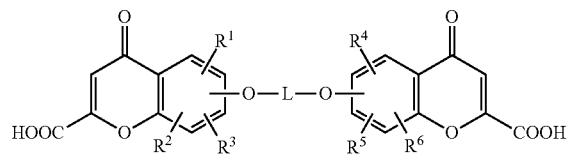

Formula I wherein:

$R^1$ is hydrogen, hydroxy, halo, lower alkyl (including substituted lower alkyl), and lower alkoxy (including substituted lower alkoxy);

$R^2$ is hydrogen, hydroxy, halo, lower alkyl (including substituted lower alkyl), and lower alkoxy (including substituted lower alkoxy);

$R^3$ is hydrogen, hydroxy, halo, lower alkyl (including substituted lower alkyl), and lower alkoxy (including substituted lower alkoxy);

$R^4$ is hydrogen, hydroxy, halo, lower alkyl (including substituted lower alkyl), and lower alkoxy (including substituted lower alkoxy);

$R^5$ is hydrogen, hydroxy, halo, lower alkyl (including substituted lower alkyl), and lower alkoxy (including substituted lower alkoxy);

$R^6$ is hydrogen, hydroxy, halo, lower alkyl (including substituted lower alkyl), and lower alkoxy (including substituted lower alkoxy); and L is an alkylene-containing linkage that may be one or the more of the following: saturated or unsaturated; substituted or unsubstituted; straight or branched; and interrupted by one or more of the moieties selected from the group consisting of carbocyclic rings, oxygen-containing heterocyclic rings, oxygen atoms, and carbonyl groups.

With respect to Formula I, in one or more embodiments it is preferred that each of $R_1$, $R_2$, $R_3$, $R_4$, $R_5$, and $R_6$ are independently selected from the group consisting of hydrogen, halogen (e.g., chloro, bromo, or iodo), lower alkyl (preferably alkyl of one to four carbon atoms, inclusive), hydroxy, or lower alkoxy (preferably alkoxy of one to four carbon atoms, inclusive).

In one or more embodiments, it is preferred that L is a selected from the group consisting of straight or branched chain polymethylene of three to seven carbon atoms, inclusive, —CH$_2$—CH=CH—CH$_2$—,

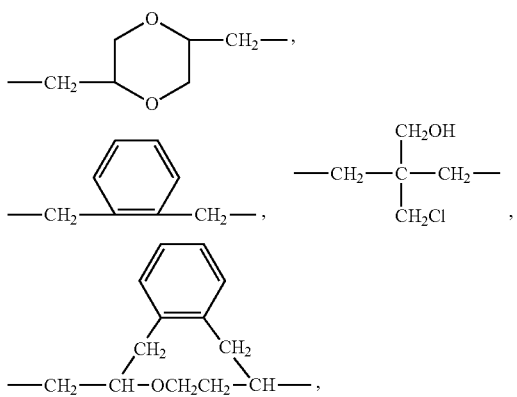

—CH₂—CH(OH)—CH₂—, —CH₂—CH(OH)—CH₂—O—CH₂—CH(OH)—CH₂—, —CH₂—O—CH₂—, —CH₂—CH₂—CH(CH₃)—CH₂—CH₂—, —CH₂—CO—CH₂— and —CH₂—CH₂—O—CH₂—CH₂—.

Compounds encompassed by Formula I can be prepared according to known methods. See, for example, U.S. Pat. No. 3,419,578 for a description of one or more methods for preparing compounds having structures encompassed by Formula I. An example of a specific bis-chromonyl compound is cromolyn, the structure of which is provided below,

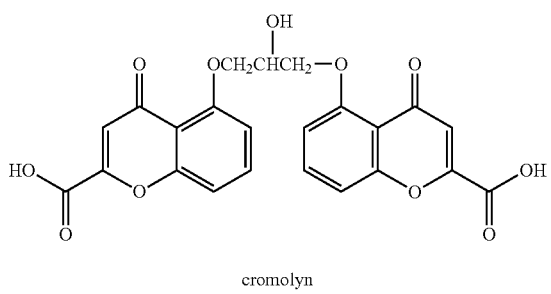

cromolyn

Each of these (and other) bis-chromonyl compounds can be covalently attached (either directly or through one or more atoms) to a water-soluble and non-peptidic oligomer.

It is believed that an advantage of the compounds of the present invention is their increased water solubility relative to the same compound lacking the water-soluble, non-peptidic oligomer(s). Although not wishing to be bound by theory, it is believed that the oligomer-containing compounds described herein, in contrast to the unconjugated "original" bis-chromonyl compound, have improved oral bioavailabilities due to the relative increase in water solubility. Even should the linkage between the residue of the bis-chromonyl compound and the oligomer be degradable, the compound still offers advantages (such as having increased absorption from the gastro-intestinal tract).

Use of oligomers (e.g., from a monodisperse or bimodal composition of oligomers, in contrast to relatively impure compositions) to form oligomer-containing compounds can advantageously alter certain properties associated with the corresponding small molecule drug, and are therefore preferred.

As indicated above, the compounds of the invention include a residue of a bis-chromonyl compound. Assays for determining whether a given bis-chromonyl compound is pharmacologically active are described in the literature. For example, assays are known that can determine whether a particular agent has activity as reducing the release of inflammation-causing compounds from mast cells.

Exemplary compounds of the invention have the following formula:

Formula I-C

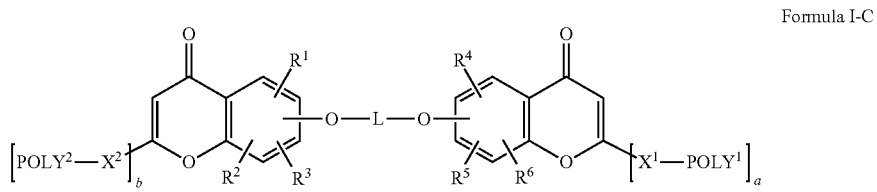

wherein:

$R^1$ is hydrogen, hydroxy, halo, lower alkyl (including substituted lower alkyl), and lower alkoxy (including substituted lower alkoxy);

$R^2$ is hydrogen, hydroxy, halo, lower alkyl (including substituted lower alkyl), and lower alkoxy (including substituted lower alkoxy);

$R^3$ is hydrogen, hydroxy, halo, lower alkyl (including substituted lower alkyl), and lower alkoxy (including substituted lower alkoxy);

$R^4$ is hydrogen, hydroxy, halo, lower alkyl (including substituted lower alkyl), and lower alkoxy (including substituted lower alkoxy);

$R^5$ is hydrogen, hydroxy, halo, lower alkyl (including substituted lower alkyl), and lower alkoxy (including substituted lower alkoxy);

$R^6$ is hydrogen, hydroxy, halo, lower alkyl (including substituted lower alkyl), and lower alkoxy (including substituted lower alkoxy);

L is an alkylene-containing linkage that may be one or the more of the following: saturated or unsaturated; substituted or unsubstituted; straight or branched; and interrupted by one or more of the moieties selected from the group consisting of carbocyclic rings, oxygen-containing heterocyclic rings, oxygen atoms, and carbonyl groups;

(a) is either zero or one, with the caveat that when (a) is zero, —$X^1$—POLY$^1$ is —COOH;

(b) is either zero or one; with the caveat that when (b) is zero, —$X^2$—POLY$^2$ is —COOH;

with the proviso that at least one of (a) and (b) is one;

$X^1$, when present, is a spacer moiety (preferably —C(O)—O—);

$X^2$, when present, is a spacer moiety (preferably —C(O)—O—);

POLY$^1$, when present, is a water-soluble, non-peptidic oligomer; and

POLY$^2$, when present, is a water-soluble, non-peptidic oligomer.

With respect to Formula I-C, in one or more embodiments it is preferred that each of $R_1$, $R_2$, $R_3$, $R_4$, $R_5$, and $R_6$ are independently selected from the group consisting of hydrogen, halogen (e.g., chloro, bromo, or iodo), lower alkyl (preferably alkyl of one to four carbon atoms, inclusive), hydroxy, or lower alkoxy (preferably alkoxy of one to four carbon atoms, inclusive).

In one or more embodiments, it is preferred that L is a selected from the group consisting of straight or branched chain polymethylene of three to seven carbon atoms, inclusive, —$CH_2$—$CH$=$CH$—$CH_2$—,

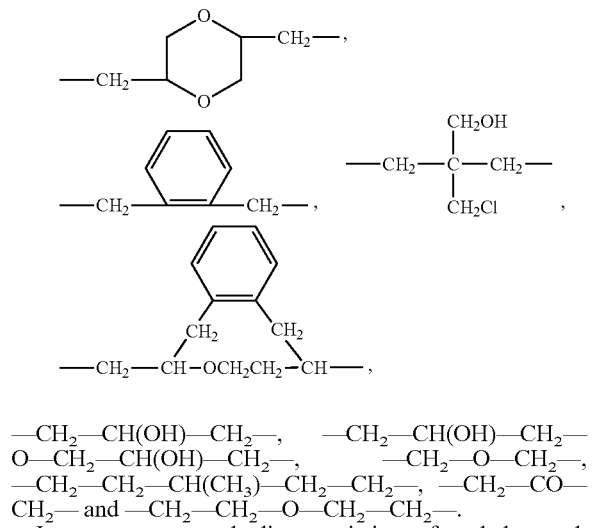

—$CH_2$—$CH(OH)$—$CH_2$—, —$CH_2$—$CH(OH)$—$CH_2$—O—$CH_2$—$CH(OH)$—$CH_2$—, —$CH_2$—O—$CH_2$—, —$CH_2$—$CH_2$—$CH(CH_3)$—$CH_2$—$CH_2$—, —$CH_2$—$CO$—$CH_2$— and —$CH_2$—$CH_2$—O—$CH_2$—$CH_2$—.

In one or more embodiments, it is preferred that each spacer moiety that is present is an ester [i.e., independently either —C(O)O— or —OC(O)—], a carbamate [e.g., independently either —NH—C(O)O— or —OC(O)—NH-] or a carbonyl. In one or more embodiments, it is preferred that only one of (a) and (b) is one. In one or more embodiments, it is preferred that both (a) and (b) are one.

Exemplary compounds of the invention are provided below.

1000 Daltons. Small molecule drugs, for the purpose of the invention, include oligopeptides, oligonucleotides, and other biomolecules having a molecular weight of less than about 1000 Daltons. Also encompassed in the term "small molecule drug" is any fragment of a peptide, protein or antibody, including native sequences and variants falling within the molecular weight range stated above. In one or more embodiments, however, it is preferred that the small molecule drug satisfies one or more of the following: not an oligopeptide; not an oligonucleotide; not an antibody; and not a fragment of any of the foregoing.

Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

The small molecule drug used in the invention, if chiral, may be obtained from a racemic mixture, or an optically active form, for example, a single optically active enantiomer, or any combination or ratio of enantiomers. In addition, the small molecule drug may possess one or more geometric isomers. With respect to geometric isomers, a composition may a mixture of two or more geometric isomers. A small molecule drug for use in the present invention may be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The bis-chromonyl compound for coupling to a water-soluble, non-peptidic oligomer possesses a free carboxyl group (a chemical "handle") suitable for covalent attachment

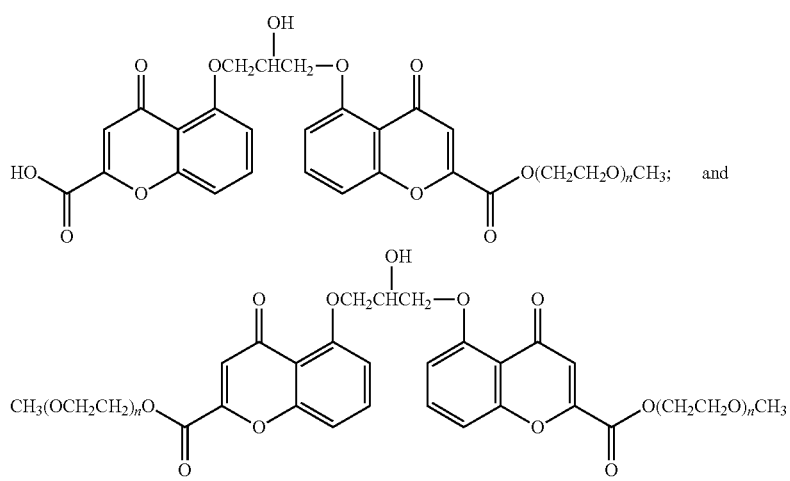

wherein, in each appearance, (n) is an integer having a value of from 2 to 30.

The bis-chromonyl compounds used in the conjugates are small molecule drugs, that is to say, pharmacologically active compounds having a molecular weight of less than about to the oligomer. In addition, the bis-chromonyl compound may be modified by introduction of a reactive group, preferably by conversion of one of its existing functional groups to a functional group suitable for formation of a stable covalent linkage between the oligomer and the drug.

The water-soluble, non-peptidic oligomer comprises one or more monomers serially attached to form a chain of monomers. The oligomer may be formed from a single monomer type (i.e., is homo-oligomeric) or two or three monomer types (i.e., is co-oligomeric). Preferably, each oligomer is a co-oligomer of two monomers or, more preferably, is a homo-oligomer.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY$^1$" and "POLY$^2$" in various structures provided herein) may have any of a number of different geometries. For example, the water-soluble, non-peptidic oligomer may be linear, branched, or forked. The water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble, non-peptidic oligomers described above.

The molecular weight of the water-soluble, non-peptidic oligomer, excluding the linker portion, is generally relatively low. Exemplary values of the molecular weight of the water-soluble, non-peptidic oligomer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers in series. In yet further embodiments, the oligomer (and the corresponding conjugate) possesses 21, 22, 23, 24, 25, 26, 27, 28, 29 or 30 monomers in series. Thus, for example, when the water-soluble and non-peptidic polymer includes $CH_3$—$(OCH_2CH_2)_n$—, "n" is an integer that may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and may fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the bis-chromonyl compound (in contrast to the step-wise addition of one or more monomers to effectively "grow" the oligomer onto the bis-chromonyl compound), it is preferred that the composition containing an activated form of the water-soluble and non-peptidic oligomer be monodispersed. In those instances, however, where a bimodal composition is employed, the composition will possess a bimodal distribution centering around any two of the above numbers of monomers. Ideally, the polydispersity index of each peak in the bimodal distribution, Mw/Mn, is 1.01 or less, and even more preferably, is 1.001 or less, and even more preferably is 1.0005 or less. More preferably, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomer units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers may be purchased or prepared from commercial sources (e.g., Sigma-Aldrich, St. Louis, Mo.), or alternatively, may be chemically synthesized. Water-soluble, non-peptidic oligomers may be prepared as described in Chen Y., Baker, G. L., J. Org. Chem., 6870-6873 (1999), WO 02/098949, and U.S. Patent Application Publication 2005/0136031.

When present, the linker or linkage (through which the water-soluble, non-peptidic polymer is attached to the bis-chromonyl compound) may be a single atom, such as an oxygen or a sulfur, two atoms, or a number of atoms. A linker may be linear in nature. The linkage, "X" can be hydrolytically stable or degradable. Preferably, the linkage "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the linker "X" comprises an ether, ester, amide, urethane, amine, thioether, urea, or a carbon-carbon bond. Functional groups such as those discussed below, are used for forming the linkages. The linkage may less preferably also comprise (or be adjacent to or flanked by) spacer groups, as described further below. Spacers are useful in instances where the bioactivity of the conjugate is significantly reduced due to the positioning of the oligomer on the parent drug.

More specifically, in selected embodiments, the linker, e.g., $X^1$, $X^2$, may be any of the following: "—" (i.e., a covalent bond, that may be stable or degradable, between the residue of the small molecule bis-chromonyl compound and the water-soluble, non-peptidic oligomer), —C(NH)NH$_2$—, —NH$_2$C(NH)—, —C(O)O—, —OC(O)—, —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R)—, R is selected from the group consisting of hydrogen, alkyl, substituted alkyl, alkenyl, substituted alkenyl, alkynyl, substituted alkynyl, aryl and substituted aryl.

For purposes of the present invention, however, a series of atoms is not considered as a linkage when the series of atoms is immediately adjacent to an oligomer segment, and the series of atoms is but another monomer such that the proposed linkage would represent a mere extension of the oligomer chain.

The linkage, e.g., $X^1$ and $X^2$, between the water-soluble, non-peptidic oligomer and the small molecule is formed by reaction of a functional group on a terminus of the oligomer (or one or more monomers when it is desired to "grow" the oligomer onto the bis-chromonyl compound) with a corresponding functional group within the bis-chromonyl compound. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A exemplary water-soluble, non-peptidic oligomer is an oligomer bearing an aldehyde functional group. In this regard, the oligomer may have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4.

Optionally, a terminus of the water-soluble, non-peptidic oligomer not bearing a functional group may be capped to render it unreactive. When the oligomer does includes a further functional group at a terminus other than that intended for formation of a conjugate, that group is either selected such that it is unreactive under the conditions of formation of the linkage or it is protected during the formation of the linkage.

As stated above, the water-soluble, non-peptidic oligomer includes at least one functional group prior to conjugation. The functional group comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Small molecule drugs for covalent attachment to an oligomer may possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the more hydrolytically stable. As mentioned above, more preferred are conjugates having a hydrolytically stable linkage between the oligomer and the drug. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e. aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, may be added, to form, for example, thioether bonds. These groups include maleimides, vinyl sulfones, vinyl pyridine, acrylates, methacrylates, and acrylamides. Other groups comprise leaving groups which may be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the bis-chromonyl compound may not have a functional group suited for conjugation. In this instance, it is possible to modify the "original" bis-chromonyl compound so that it does have a functional group suited for conjugation. For example, if the bis-chromonyl compound has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule bis-chromonyl compound bearing a carboxyl group wherein the carboxyl group-bearing small molecule bis-chromonyl compound is coupled to an amino-terminated oligomeric ethylene glycol, to provide a conjugate having an amide group covalently linking the small molecule bis-chromonyl compound to the oligomer. This can be performed, for example, by combining the carboxyl group-bearing small molecule bis-chromonyl compound with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule bis-chromonyl compound bearing a hydroxyl group wherein the hydroxyl group-bearing small molecule bis-chromonyl compound is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

In another example, it is possible to prepare a conjugate of a small molecule bis-chromonyl compound bearing a ketone group by first reducing the ketone group to form the corresponding hydroxyl group. Thereafter, the small molecule bis-chromonyl compound now bearing a hydroxyl group can be coupled as described herein.

In still another instance, it is possible to prepare a conjugate of a small molecule bis-chromonyl compound bearing an amine group. In one approach, the amine group-bearing small molecule bis-chromonyl compound and an aldehyde-bearing oligomer are dissolved in a suitable buffer after which a suitable reducing agent (e.g., NaCNBH$_3$) is added. Following reduction, the result is an amine linkage formed between the amine group of the amine group-containing small molecule bis-chromonyl compound and the carbonyl carbon of the aldehyde-bearing oligomer.

In another approach for preparing a conjugate of a small molecule bis-chromonyl compound bearing an amine group, a carboxylic acid-bearing oligomer and the amine group-bearing small molecule bis-chromonyl compound are combined in the presence of a coupling reagent (e.g., DCC). The result is an amide linkage formed between the amine group of the amine group-containing small molecule bis-chromonyl compound and the carbonyl of the carboxylic acid-bearing oligomer.

One of ordinary skill in the art, using routine experimentation, may determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) may also be used to study oral drug transport. In addition, non-in vivo methods include rodent everted gut excised tissue and Caco-2 cell monolayer tissue-culture models. These models are useful in predicting oral drug bioavailability.

The present invention also includes pharmaceutical preparations comprising a conjugate as provided herein in combination with a pharmaceutical excipient. Generally, the conjugate itself may be in a solid form (e.g., a precipitate), which may be combined with a suitable pharmaceutical excipient that may be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient may also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant may be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in a preparation of the compounds of the invention. Nonlimiting examples of acids that may be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition may vary depending on a number of factors, but may optimally be a therapeutically effective dose when the composition is stored in a unit dose container. A therapeutically effective dose may be determined experimentally by repeated administration of increasing amounts of the conjugate in order to determine which amount produces a clinically desired endpoint.

The amount of any individual excipient in the composition may vary depending on the activity of the excipient and particular needs of the composition. The optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

The excipient may be present in the composition in an amount of about 1% to about 99% by weight, preferably from about 5%-98% by weight, more preferably from about 15-95% by weight of the excipient, with concentrations less than 30% by weight more preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions may take any number of forms and the invention is not limited in this regard. Exemplary preparations are more preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and may also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, may be manufactured using standard tablet processing procedures and equipment. Direct compression and granulation techniques are preferred when preparing tablets or caplets containing the conjugates described herein. In addition to the conjugate, the tablets and caplets may generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition may be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (as a lyophilizate or precipitate, which may be in the form of a powder or cake), as well as formulations prepared for injection, which are liquid and require the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration may take the form of nonaqueous solutions, suspensions, or emulsions, each being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein may also contain adjuvants such as preserving, wetting, emulsifying, and dispersing agents. The formulations are rendered sterile by incorporation of a sterilizing agent, filtration through a bacteria-retaining filter, irradiation, or heat.

The conjugate may also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure may contain a single or multiple reservoirs.

The conjugate may also be formulated into a suppository for rectal administration. With respect to suppositories, the conjugate is mixed with a suppository base material (e.g., an excipient that remains solid at room temperature but softens, melts or dissolves at body temperature) such as coca butter (theobroma oil), polyethylene glycols, glycerinated gelatin, fatty acids, and combinations thereof. Suppositories may be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

The method may be used to treat any condition that may be remedied or prevented by administration of the particular conjugate. Those of ordinary skill in the art appreciate which conditions a specific conjugate may effectively treat. The actual dose to be administered may vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount may range from about 0.001 mg to 1000 mg, preferably in doses from 0.01 mg/day to 750 mg/day, and more preferably in doses from 0.10 mg/day to 500 mg/day.

The unit dosage of any given conjugate may be administered in a variety of dosing schedules depending on the judgment of the clinician, needs of the patient, and so forth. The specific dosing schedule may be known by those of ordinary skill in the art or may be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are incorporated by reference in their entireties.

EXPERIMENTAL

It is to be understood that while the invention has been described in conjunction with certain preferred and specific embodiments, the foregoing description as well as the example that follows are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data was generated by a 300 MHz or greater NMR spectrometer manufactured by Bruker. A list of certain compounds as well as the source of the compounds is provided below.

Example 1

A conjugate was prepared in accordance with the schematic provided below.

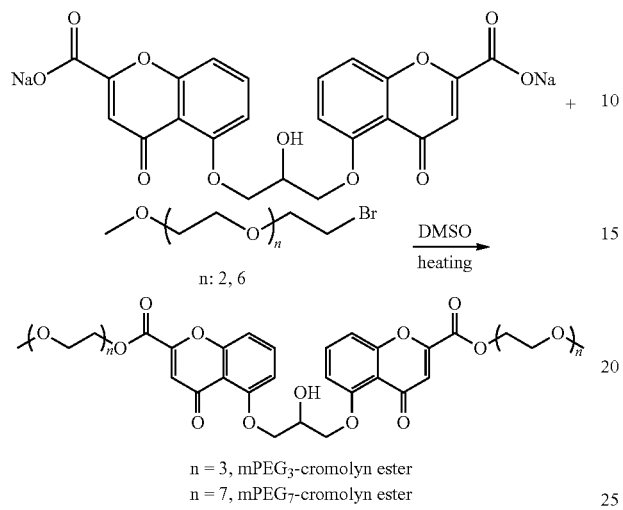

n = 3, mPEG₃-cromolyn ester
n = 7, mPEG₇-cromolyn ester

The materials used in carrying out Example 1 were as follow: cromolyn sodium: Sigma-Aldrich (St. Louis, Mo.), minimum 95% pure, catalog number. C0399-25g, lot no: 035K0967; DMSO: Aldrich (St. Louis, Mo.), catalog number 276855-100 mL, lot number: 06054KD; mPEG$_n$-Br, prepared in accordance with literature.

Synthesis of mPEG₃-Cromolyn Ester

Cromolyn sodium (1.07 g, 1.98 mmol) was placed into a 50 mL-round flask and then anhydrous DMSO (16 mL) was added. The mixture was heated at 60° C. for 15 minutes, more DMSO (10 mL) was added. After thirty minutes at 80° C., mPEG₃-Br (1.655 g, 7.29 mmol) was added. The resulting mixture was stirred at 70° C. for an additional seven hours, then stored at room temperature overnight, and then at 70° C. for another 2.5 hours. The solvent was removed under high vacuum at 70-80° C. The residue was mixed with water and dichloromethane. About 2 mL of 1N HCl was added. The organic phase was separated and the aqueous solution was extracted with DCM (2×40 mL). The combined organic phases were concentrated and the resulting residue was purified by column chromatography on silica gel to afford 0.5979 g of product in 38% yield. ¹H-NMR (CDCl₃) δ 7.58 (t, J=8.4 Hz, 2H), 7.15 (d, J=8.1 Hz, 2H), 6.97 (d,s), 6.95 (d, J=8.4 Hz, 2H), 4.58-4.45 (m, 8H), 4.36-4.31 (m, 2H), 3.84-3.52 (m, 20H), 3.34 (s, 6H). LC-MS: 761.2 (MH⁺/z, 100%).

Synthesis of mPEG₇-Cromolyn Ester mPEG₇-Br (3.0916 g, 7.67 mmol) was added to a mixture of cromolyn sodium (1.297 g, 2.405 mmol) in anhydrous DMSO at 80° C. (oil temperature). The resulting mixture was stirred at 80° C. for seven hours, then at room temperature overnight, and at 80° C. for another 1.5 hours. The solvent was removed under high vacuum at 70-80° C. The residue was mixed with 1 N HCl (~4 mL) and dichloromethane. Water was added to dilute. The organic phase was separated and the aqueous solution was extracted with DCM (3×100 mL). The combined organic phases were concentrated. The residue was purified by column chromatography twice on silica gel and preparative TLC to afford 40 mg of product. ¹H-NMR (CDCl₃) δ7.58 (t, J=8.1-88.4 Hz, 2H), 7.14 (d, J=8.4 Hz, 2H), 6.95 (d,s), 6.93 (d, J=9.0 Hz, 2H), 4.56-4.46 (m, 8H), 4.35-4.30 (m, 2H), 3.82-3.44 (m, 46H), 3.34 (s, 6H). LC-MS: 761.2 (MH⁺/z, 100%). LC-MS: 1113.4 (NH⁺), 1135.4 (MNa⁺).

What is claimed is:

1. A compound according to the following formula:

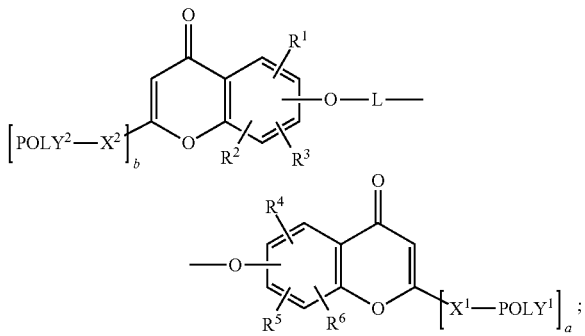
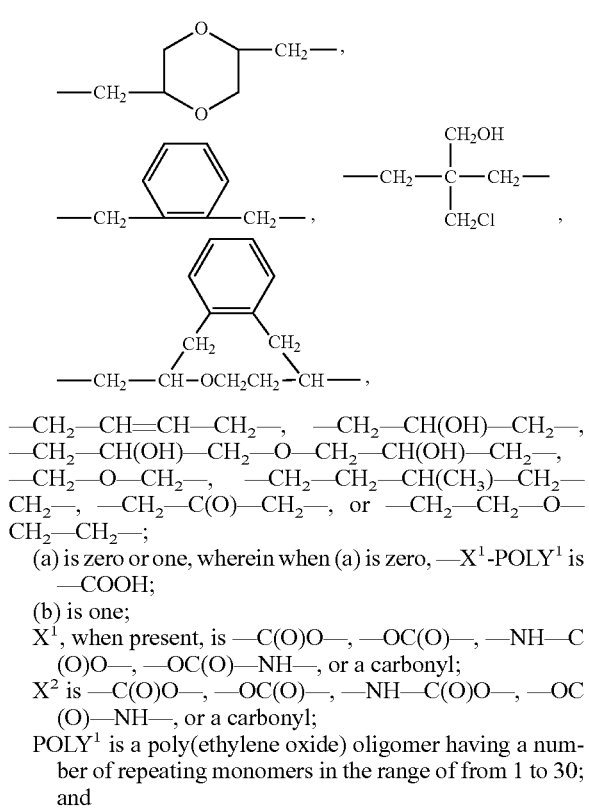

wherein:
R¹ is hydrogen, hydroxy, halo, lower alkyl, or lower alkoxy;
R² is hydrogen, hydroxy, halo, lower alkyl, or lower alkoxy;
R³ is hydrogen, hydroxy, halo, lower alkyl, or lower alkoxy;
R⁴ is hydrogen, hydroxy, halo, lower alkyl, or lower alkoxy;
R⁵ is hydrogen, hydroxy, halo, lower alkyl, or lower alkoxy;
R⁶ is hydrogen, hydroxy, halo, lower alkyl, or lower alkoxy;
L is —CH₂—CH═CH—CH₂—, —CH₂—CH(OH)—CH₂—, —CH₂—CH(OH)—CH₂—O—CH₂—CH(OH)—CH₂—, —CH₂—O—CH₂—, —CH₂—CH₂—CH(CH₃)—CH₂—CH₂—, —CH₂—C(O)—CH₂—, or —CH₂—CH₂—O—CH₂—CH₂—;

(a) is zero or one, wherein when (a) is zero, —X¹-POLY¹ is —COOH;
(b) is one;
X¹, when present, is —C(O)O—, —OC(O)—, —NH—C(O)O—, —OC(O)—NH—, or a carbonyl;
X² is —C(O)O—, —OC(O)—, —NH—C(O)O—, —OC(O)—NH—, or a carbonyl;
POLY¹ is a poly(ethylene oxide) oligomer having a number of repeating monomers in the range of from 1 to 30; and POLY² is a poly(ethylene oxide) oligomer having a number of repeating monomers in the range of from 1 to 30.

2. The compound of claim 1, wherein L is —CH₂—CH(OH)—CH₂—.

3. The compound of claim 1, having the formula:

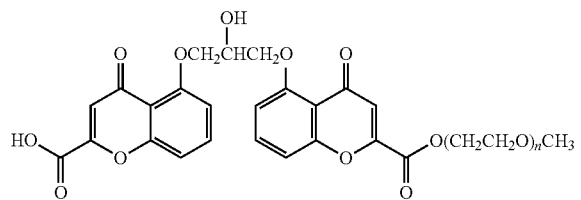

wherein (n) is an integer from 2 to 30.

4. The compound of claim 1, wherein each poly(ethylene oxide) oligomer has a number of repeating monomers in the range of from 1 to 10.

5. The compound of claim 1, wherein each poly(ethylene oxide) includes an alkoxy or hydroxy end-capping moiety.

6. A composition comprising: (i) a compound of claim 1; and (ii) a pharmaceutically acceptable excipient.

7. A composition of matter comprising a compound of claim 1 present in a dosage form.

8. A method of treating asthma, allergic rhinitis, allergic conjunctivitis, mastocytosis, dermatographic urticaria, or ulcerative colitis comprising administering to a subject a compound of claim 1.

* * * * *